United States Patent [19]

Schmidt

[11] 4,093,765

[45] June 6, 1978

[54] SOFT ABSORBENT FIBROUS WEB AND DISPOSABLE DIAPER INCLUDING SAME

[75] Inventor: Frank P. Schmidt, Cheltenham Township, Montgomery County, Pa.

[73] Assignee: Scott Paper Company, Philadelphia, Pa.

[21] Appl. No.: 657,893

[22] Filed: Feb. 13, 1976

[51] Int. Cl.$^2$ .................... A61F 13/16; A61F 13/18; A61F 13/20; B32B 3/10

[52] U.S. Cl. .................... 428/134; 128/184; 128/290 R; 128/290 P; 128/296; 162/112; 428/138; 428/152; 428/195; 428/198; 428/318

[58] Field of Search .............. 162/111, 112; 128/284, 128/290 R, 290 P, 296; 428/134, 138, 152, 195, 198, 318

[56] References Cited

U.S. PATENT DOCUMENTS

| | | | |
|---|---|---|---|
| Re. 27,453 | 8/1972 | Schutte et al. | 162/111 |
| 3,484,594 | 11/1974 | Buell | 128/284 |
| 3,817,827 | 6/1974 | Benz | 162/111 |
| 3,821,068 | 6/1914 | Shaw | 162/111 |
| 3,879,257 | 4/1975 | Gentile et al. | 428/198 |
| 3,903,342 | 9/1975 | Roberts | 428/198 |
| 3,908,058 | 9/1975 | Russell et al. | 428/198 |
| 3,973,067 | 8/1976 | Newman | 428/195 |

FOREIGN PATENT DOCUMENTS

| | | | |
|---|---|---|---|
| 1,294,794 | 11/1972 | United Kingdom | 162/111 |

*Primary Examiner*—J.C. Cannon
*Attorney, Agent, or Firm*—Martin L. Faigus; William J. Foley

[57] ABSTRACT

A soft, absorbent fibrous web is formed from an aqueous slurry and includes randomly arranged and contacting wood pulp fibers produced by the sulfate process which constitute the predominate fiber component, by weight, of the web. A portion of the web thickness is substantially free of debonders and wet strength additives, and the fibers in that portion of the web are held together almost exclusively by papermaking bonds. A plurality of partially fractured areas are provided in spaced-apart regions which are substantially uniformly distributed throughout the web. An adhesive bonding material extends only partially through the web thickness to form adhesively bonded regions having a greater strength than underlying regions which are bonded together almost exclusively by the papermaking bonds. The web of this invention has a basis weight in the range of from about 25 to about 100 lbs/2,880 feet$^2$, a density of from about 0.08 grams/cc to less than about 0.16 grams/cc. a liquid holding capacity of greater than 500%, an absorbency rate of less than 2.5 seconds, a wicking rate of greater than 14 cm/10 minutes and a wet-cross-machine-direction tensile strength of greater than 2 oz./inch. Preferably the fibrous web is employed as a wicking layer beneath a low density fluff batt in a disposable diaper or similar disposable sanitary product.

16 Claims, 8 Drawing Figures

SOFT ABSORBENT FIBROUS WEB AND DISPOSABLE DIAPER INCLUDING SAME

BACKGROUND OF THE INVENTION

1. Field of the Invention

This invention relates to a soft, absorbent fibrous web, and more specifically, to a fibrous web having a balance of properties which makes it highly desirable for use as a wicking layer in a disposable diaper and similar disposable sanitary products.

2. Description of the Prior Art

Disposable absorbent articles, such as disposable diapers, are exceedingly popular today. Most of the commercially available disposable diapers employ a low density batt of cellulosic fibers as the primary absorbent component. These batts have a high liquid holding capacity; however, due to their loosely formed, low density construction they are exceedingly weak and are not effective in wicking (i.e. distributing) fluids laterally. Accordingly, a localized flooding of the fibrous batt can take place in the area in which the urine is initially introduced. This can cause undesirable leakage of body fluid from the diaper prior to utilizing a significant portion of the absorptive capacity of the fibrous batt. To overcome the problem of localized flooding it is well-known to employ a wicking layer adjacent to the surface of the fibrous batt which is most remote from the wearer. The wicking layer is more dense that the fibrous batt, and functions to receive body fluids which pass through the batt, and thereafter to wick the body fluids laterally for subsequent absorption into dry areas of said batt. Accordingly, a wicking layer is employed to transmit fluids laterally to improve the utilization of the absorptive capacity of the diaper.

An effective wicking layer should have the ability to quickly absorb liquids which pass through the absorbent batt, and thereafter to rapidly direct the fluids laterally to prevent localized flooding of said batt. Moreover, the wicking layer should have a high liquid holding capacity to cooperate with the absorbent batt in retaining body fluids. Providing a high liquid holding capacity in the wicking layer allows one to reduce the total weight of absorbent fibers employed in the low density batt. Accordingly, it makes sense to design the wicking layer so that it can also retain a significant volume of body fluid.

It is well known that the structural characteristics of a web which provide for a high liquid holding capacity generally are inconsistent with the structural characteristics required to achieve rapid wicking of fluids laterally throughout the web. Accordingly, people skilled in the art have always been faced with the problem of achieving a desired balance between wicking rate and liquid holding capacity in wicking layer structures.

A well-designed wicking layer should also have the ability to retain its structural integrity when wet. This requirement should be fairly obvious in view of the fact that the wicking layer functions in a liquid environment. If the wicking layer falls apart in the presence of liquids it will lose at least some of its ability to retain and wick liquids. Unfortunately, wet strength additives generally reduce the wicking characteristics of a fibrous structure. Moreover, wet strength additives tend to impart stiffness, rather than softness to a fibrous web structure. Accordingly, it is highly desirable to include a wet strength additive in a wicking layer in a manner which does not seriously impair it wicking characteristics, and does not significantly increase its stiffness.

The prior art suggests forming wicking layers by both dry forming and wet forming techniques. The dry formed wicking layers are generally formed by separating the fibers from dense pulp lap, and conveying the fibers in air to a foraminous forming surface upon which a low density fibrous web is deposited. The web is then compacted, or embossed to provide a desired density in the structure to enhance its wicking rate characteristics. Also, it is common to add a wet strength additive, such as a resin binder, to prevent the web from falling apart during its use. It is also common practice to include debonders in the pulp lap to minimize interfiber bonding. By minimizing the interfiber bonding the energy required to separate the fibers from the feed mat is reduced, and the separation of individual fibers from the feed mat is enhanced. Unfortunately these debonders generally have an adverse effect on the wicking characteristics of the fibrous web formed from the pulp lap.

Air-laid wicking layers are formed at a considerably slower speed than wet-formed wicking layers. This lower formation speed generally results in an increased cost of manufacturing. In view of the fact that disposable, or limited use articles preferably should be low cost items, it is highly desirable to minimize the cost of the components employed to manufacture such disposable articles. Accordingly, it is believed to be more desirable to form the wicking layer as a wet-laid structure at papermaking speeds in the range of from about 1,500 to 5,000 feet/minute, than by an air-lay process which is run at speeds considerably below 1,000 feet/minute.

The prior art suggests wet-laid sheets for use in enhancing fluid distribution in disposable diapers. One well known wet-laid construction is in the form of a creped web of cellulosic wadding formed by a conventional papermaking operation. In that operation the web generally is highly compressed as it is transferred between sections of the papermaking machine while it still has a moisture level of greater than 20%. The high compaction of the web at this moisture level results in excessive hydrate bonding and densification of the web. This adversely effects the wicking rate, absorbency rate and softness characteristics of the web. Moreover, a web which is excessively densified will not respond satisfactorily to post treatment operations employed to attempt to optimize the above properties.

In addition to the prior art discussed above, British patent specification No. 1,294,794 and U.S. Pat No. Re. 27,453; U.S. Pat. Nos. 3,817,827; 3,821,068 and 3,879,257 are considered relevant to the instant invention. However, none of these references, taken singly or in combination, teach the unique combination of product attributes in accordance with the instant invention.

From the above discussion it should be apparent that there is a need in the art for a soft and absorbent wet formed fibrous structure having a better balance of properties for use as a wicking layer than has been achieved in the past. This invention relates to such an improved wet formed fibrous structure.

SUMMARY OF THE INVENTION

This invention relates to a soft, absorbent fibrous web which is particularly adapted for use as a wicking layer in disposable diapers and similar disposable sanitary products. The fibrous web is formed from an aqueous slurry which is substantially free of debonders and wet strength additives, and the predominate fiber component of the slurry, by weight, is wood pulp fibers made by the sulfate process (hereinaffer referred to as "sulfate wood pulp fibers"). The fibers in the initially formed and dried web are bonded together almost exclusively by papermaking bonds. A plurality of partially fractured areas are provided in spaced-apart regions which are substantially uniformly distributed throughout the web. An adhesive bonding material extends only partially through the web to provide adhesively bonded regions having a greater strength than underlying regions which are bonded together almost exclusively by the papermaking bonds. The web has a basis weight in the range of from about 25 to about 100 lbs/2,880 feet$^2$, a density of from about 0.08 grams/cc to less than about 0.16 grams/cc, a liquid holding capacity of greater than 500%, an absorbency rate of less than 2.5 seconds, a wicking rate of greater than 14 cm/10 minutes and a wet-cross-machine-direction tensile strength of greater than 2 oz./inch. The balance of properties achieved in the web of this invention renders it highly suitable for use as a wicking layer in disposable diapers, and similar disposable sanitary products.

The term "partially fractured" when used in the specification and claims of this application shall mean mechanical working of the web in some locations at least to the degree of breaking some of the bonds holding the fibers to each other, and may include working the sheet to the extent that the web is completely torn in portions of the working locations to the point of forming cuts or apertures in the web.

Reference to "debonders" and "wet strength additives" throughout this application relates to the class of debonders and wet strength additives which adversely effect wicking rate and/or absorbency rate in fibrous structures. Representative debonders within this class are cationic ammonium compounds, such as QUAKER 2000 and QUAKER 2003 available from Quaker Chemical Corporation of Conshohocken, PA, and RYCOFAX 613 and RYCOFAX 637 available from Reichold Inc. of Conshohocken, PA. Many other debonders are within this class, and can easily be determined experimentally by people skilled in the art. Representative wet strength additives within this class are urea formaldehyde and melamine formaldehyde resins. Many other wet strength additives are also within this class, and can easily be determined experimentally by people skilled in the art.

In the preferred embodiment of this invention the adhesive bonding material is applied to only one side of the web, preferably in a fine spaced-apart pattern, and the web is adhered to a creping surface by the bonding material and creped therefrom by a creping doctor blade. The creping action softens the web, and in addition increases the extensibility of said web by foreshortening it. The foreshortening of the web provides relatively coarse ridges on the surface of the web which is not adhered to the creping surface. The creping operation is carried out to provide a minimum stretch of 10%, and most preferably greater than 14%, in the direction of the web transverse to the machine direction of web formation. The softening of the web in conjunction with the increase in extensibility of the web enhances the hand of said web. The preferred method of pattern creping the fibrous webs of this invention is set forth in British patent specification No. 1,294,794, assigned to Scott Paper Company. That patent is incorporated by reference into the instant application.

The major factors contributing to the high wicking rate in the fibrous web of this invention are the composition of the slurry (i.e., free of debonders and wet strength additives and including predominately sulfate wood pulp fibers), and the density of the web. The major factor in achieving the desired density range in the fibrous web of this invention is the manner in which the web is formed and dried to provide the papermaking bonds which initially hold the web together. In accordance with this invention the web is formed and dried to a predetermined dryness level without being subjected to significant mechanical compression. This method of forming and drying a fibrous web is fully disclosed in U.S. Pat. No. 3,821,068, assigned to Scott Paper Company, and is incorporated by reference into the instant application.

The high fluid holding capacity of the web of this invention is provided by its basis weight range, and the partial fracturing of the sheet. Most preferably the sheet is fractured by the embossing method disclosed in U.S. Pat. No. Re. 27,453, assigned to Scott Paper Company to provide cuts, or apertures completely through the sheet thickness. That patent is incorporated by reference into the instant application.

The combination of the embossy operation and creping operation carried out in accordance with the preferred embodiment of this invention are primarily responsible for increasing the overall wet strength and softness of the web without having a significant adverse effect on its wicking rate characteristics.

The web of this invention has an excellent balance among softness, fluid holding capacity, absorbency rate, wicking rate and strength which has not been achieved in prior art wet formed paper products in the basis weight range of the web of this invention.

Further object and advantages of this invention will become apparent upon reading the detailed description which follows, taken in conjunction with the drawings.

DESCRIPTION OF THE PREFERRED EMBODIMENT OF THE INVENTION

Figure 1:
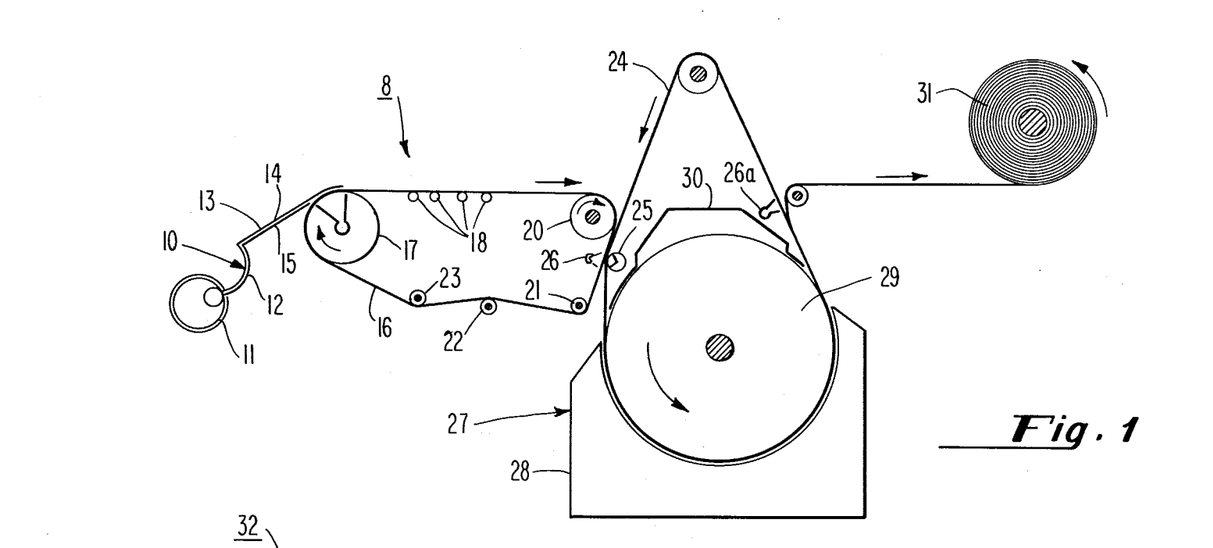
FIG. 1 is a schematic side elevation view of a papermaking machine which can be employed in the formation of the fibrous web of this invention.

Referring to FIG. 1, a papermaking apparatus employed in the formation of the fibrous web of this invention is indicated generally by the reference numeral 8. The apparatus includes a stock distribution means 10 for delivering an aqueous papermaking slurry or fiber furnish to a Fourdrinier wire 16. The stock distribution means includes a tapered manifold or header 11 which is connected to a source (not shown) of the aqueous papermaking slurry or fiber furnish. A number of branch tubes or laterals 12 connect the tapered manifold 11 to blending chamber 13 defined by generally parallel, upper and lower walls 14 and 15. The stock distribution system 10 may be similar to that disclosed in U.S. Pat. No. 3,298,905.

It is extremely important to this invention that the papermaking slurry be substantially free of debonders and wet strength additives which have an adverse effect on the wicking rate and/or absorbency rate of the formed web. Moreover, the predominate fiber component of the slurry, preferably over 80% by weight, is Kraft, or sulfate wood pulp fibers. The sulfate process for forming dense wood pulp laps or sheets is extremely efficient in removing undesirable impurities from the fibers during the pulping operation. These impurities would have an adverse effect on the wicking rate characteristics of the formed web if left in the pulp lap. The fiber furnish can be a blend of softwood and hardwood fibers, with the most preferred furnish being 100% sulfate softwood fibers.

The Fourdrinier wire 16 is carried over a suction breast roll 17 and over a plurality of table rolls 18, after which it passes around a wire turning roll 20 and is threaded past three guide rolls 21, 22 and 23 and back to the suction breast roll 17. The Fourdrinier wire 16 and its supporting rolls is driven by a drive means (not shown) connected to the wire turning roll 20.

One or more vacuum boxes, hydrofoils or other dewatering or formation assisting devices (none of which are shown in FIG. 1) may be employed in conjunction with the Fourdrinier wire 16. In addition, the configuration of the papermaking machine may vary widely from that described above without having any effect upon the present invention. However, it is highly desirable that the web thus formed on the Fourdrinier wire 16, or other foraminous surface, be maintained virtually free from any mechanical compression or compaction until it is at least 80 percent dry.

After the slurry is deposited on the Fourdrinier wire 16 and dewatered sufficiently to form a web, the web is transferred, substantially free from any compaction or mechanical compression, from the upper surface of the Fourdrinier wire 16 to the surface of a foraminous drying fabric 24. The drying fabric 24 may comprise a woven sheet material, such as made from wire or other filamentary materials, or a perforated or foraminous base. The drying fabric 24 is advanced past the position closely adjacent the portion of the Fourdrinier wire 16 running between the wire turning roll 20 and the first guide roll 21. In doing so, it passes over a rotating suction pickup roll 25 or a stationary suction pickup shoe, and transfer of the web to the drying fabric 24 at this location may be assisted, if desired, by a steam or air jet, such as might isssue from a header 26 disposed opposite the Fourdrinier wire 16 and the suction pickup roll 25.

The drying fabric 24 carrying the web moves from the suction pickup roll 25 into the drying means, indicated generally by reference numeral 27. The drying means 27 may comprise any means for preferably drying, without compressing, a web to a point where it has a moisture content of preferably less than 20 percent by weight, that is, so that it is more than 80 percent dry. Various techniques for drying the web may be employed, such as radiant heat lamps, tunnel dryers, or transpiration dryers wherein air, preferably heated, is passed through the web. FIG. 1 illustrates a typical form of transpiration dryer in which air from a hood 28 is passed through the web, through the drying fabric 24, and through the drum 29 which supports both the web and the drying fabric 24. The air is then removed from the interior of the drum 29 by another hood 30. A typical form of such drying apparatus is shown in U.S. Pat. No. 3,432,936. In the most preferred embodiment of the invention the web is completely dried in the drying means 27 and is wound into a roll 31. The web transfer from the drying fabric 24 to roll 31 can be initiated by an air jet issuing from header 26a.

In practicing the invention, it would be ideal to avoid all mechanical pressing on the web until it is dry enough to not form significantly more papermaking bonds upon being compressed. However, it is impracticable to avoid small amounts of pressure at some locations in the apparatus, such as where the Fourdrinier wire 16 comes together with the drying fabric 24. But, in accordance with the preferred practice of the invention, the pressure applied at such locations in the apparatus is sufficiently low to avoid excessive compaction of the web. As an illustration, the pressure applied to the web at all locations in the apparatus preferably is less than 5 psi. In comparison, a conventional press operation, as used in the prior art, applies a pressure to the web of up to several hundred psi.

The web formed thus far is held together almost exclusively by the hydrate bonds associated with the papermaking process. This web has excellent absorbency and wicking rate characteristics, which are due to the capillary structure (i.e. density), fiber composition, and freeness of the web from debonders and wet strength additives. However, the web formed at this stage of the process does not have the desired softness, fluid holding capacity and wet strength levels for use as a wicking layer in disposable diapers and similar disposable articles.

Figure 2:
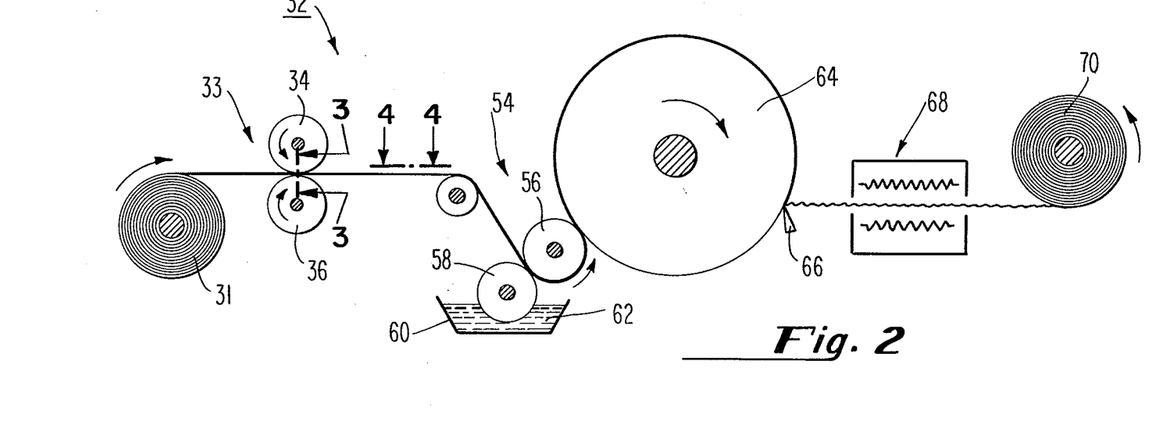
FIG. 2 is a schematic side elevation view of a post-treating apparatus which can be employed in the formation of the fibrous web of this invention.

Referring to FIG. 2, a post-treatment apparatus for improving the softness, fluid holding capacity and wet strength levels of the web is indicated generally by the reference numeral 32. If desired, the post-treatment apparatus 32 could form an extension of the papermaking machine 8. In that case the web would not be wound into a roll 31, but would be conveyed directly from the dryer 27 to the post treatment operations.

The apparatus 32 includes an embossing station 33. The embossing station 33 is similar to that disclosed in U.S. Pat. No. Re. 27,453, and is employed to increase the softness of the web without adversely affecting the wicking rate, absorbency and capacity characteristics of said web. The embossing operation performed at station 32 enhances web softness by reducing the tensile strength and increasing the caliper (thickness) of the web.

Figure 3:
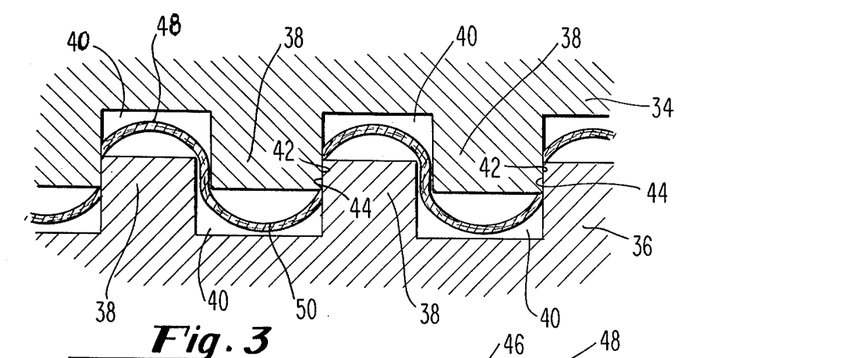
FIG. 3 is a sectional view along line 3—3 of FIG. 2.

Referring to FIGS. 2 and 3 the embossing station 33 includes opposed rolls 34 and 36 providing an embossing nip between them. The rolls 34 and 36 preferably are interconnected (as through suitable gears, not shown) so that they rotate in synchronism.

It is preferred that the upper roll 34 be supported with its surface in spaced relation to the surface of the lower roll 36. This will prevent the rolls from contacting, and thereby will reduce wear on the roll surfaces and prevent the entire surface of the fibrous web from being compressed.

The rolls 34 and 36 are designed generally to compress a predetermined amount of the surface are of the web and to stretch portions of the web between the compressed areas beyond the elastic limit of the web whereby more or less to separate the fibers from one another and thereby increase the softness and fluid holding capacity of the web. The compressed area is less than 50% of the total paper area and preferably is approximately 10%. The rolls 34 and 36 are each formed with many projections 38 and depressions 40. The projections 38 preferably are formed by machining or engraving the roll surfaces. The projections on each roll are generally in alignment with the depressions on the other roll (FIG. 3), and preferably have a mesh range of 6 × 6 to 24 × 24. This mesh range provides from 18 to 288 projections and depressions per square inch of the roll surfaces.

Referring to FIG. 3, the amplitude of the undulations in each roll is greater than the thickness of the web, and when the web is fed between the rolls, it is pushed by the projections 38 on one roll into the depressions 40 on the other roll. Preferably the clearance between the projections 38 and the valley of the juxtaposed depressions 40 exceeds the thickness of the web and the web is not compressed in these areas. However, along side walls of the undulations the so-deformed web is stretched beyond its modulus of elasticity and is deformed. In fact, surfaces 42 and 44 of adjacent projection of the rolls are positioned sufficiently close to each other to cut the web completely through its thickness in the form of narrow slits, or apertures, as indicated by numeral 46 in FIG. 4. For further details relating to an embossing technique similar to that described above reference should be had to U.S. Pat. No. Re. 27,453, which has already been incorporated by reference into this application.

At this point in the operation the sheet has excellent wicking, absorbency, softness and capacity characteristics. However, the sheet has an exceedingly low wet tensile strength and may fall apart if used as a wicking layer in disposable diapers. The final processing step of this invention relates to imparting sufficient wet tensile strength to the sheet so that it will not fall apart when subjected to body fluids. The property which is important in this regard is the wet tensile strength in the sheet in the direction transverse to the machine-direction of sheet formation, since the tensile strength in the transverse direction (i.e. cross-machine-direction) is generally lower than that in the machine-direction. Accordingly, if the cross-machine-direction wet tensile strength is adequate to prevent the web from falling apart, the web will be suitable for its intended function.

Figure 4:
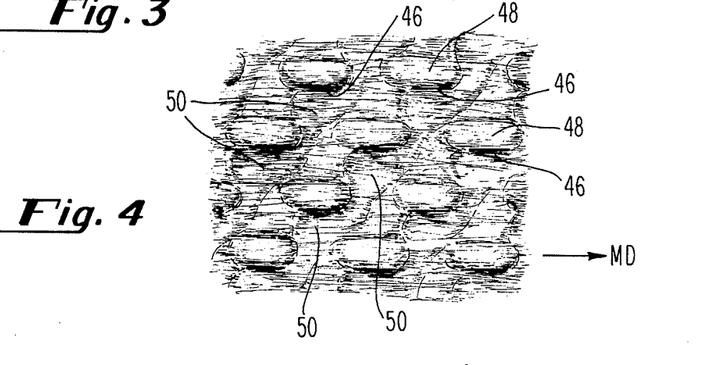
FIG. 4 is a greatly enlarged fragmentary plan view of the web of this invention in an intermediate stage of its formation, and is taken along line 4—4 of FIG. 2.

Referring to FIGS. 3 and 4, the embossed web has a plurality of crests 48 and valleys 50 on each side thereof; the crests on one side forming the depressions on the other side. The cuts 46 are formed in side surfaces which connect adjacent crests and valleys together.

Referring again to FIG. 2, the post-treatment apparatus 32 preferably includes a pattern-crepe station 54 of the type disclosed in Bristish Pat. No. 1,294,794. That patent has already been incorporated by reference into the instant application, but for purposes of completeness the pattern-crepe operation will be described herein.

After the embossing operation at station 33, the web is fed into a nip formed by a smooth rubber press roll 56 and a patterned metal rotogravure rull 58. The lower transverse portion of the rotogravure roll 58 is disposed in a pan 60 containing bonding material 62. In this manner, bonding material is applied to one surface of the web to form bonded web portions in which fibers are bonded together at least at certain portions along their length.

Preferably the bonding material is applied in a fine pattern which leaves a substantial portion of the surface of the web free from bonding material, for example the bonding material may be applied in a discontinous predetermined intermittent pattern of discrete solid area. Most preferably the pattern comprises less than 35% of the total surface area of the web so as to leave 65% or more of the surface of the web free from bonding material, at least when printed. Thus, any of the patterns taught by U.S. Pat. Nos. 3,047,444; 3,009,822: 3,059,313: and 3,009,823 may be advantageously employed. Some migration of bonding material occurs after printing. However, the bonding material is applied to only penetrate partially through the thickness of the web. Preferably lateral migration in all directions in the plane of the web is minimized so as to leave areas comprising a substantial portion of the web free from any bonding material.

The web issuing from the nip between rolls 56 and 58 with bonding material on one of its surfaces is then fed around the press roll 56 and brought into engagement with the surface of a rotatable creping drum 64. The creping drum 64 usually comprises a heated pressure vessel such as a Yankee dryer. The creping drum is characterized by an extremely smooth, polished surface to which the bonding material, applied to the web, adheres. The level of heating depends upon both the characteristics of the particular bonding material employed and the moisture level in the web.

The web is carried on the surface of the creping drum 64 for a distance, and then is removed therefrom by the action of a creping doctor blade 66. The web can then be directed to a heating station 68 at which the drying of the web is completed, and the bonding material is cured or set. The web is then directed into a roll 70.

The adhesive bonding material employed in the pattern crepe operation must be capable of at least two functions, one being the ability to bond fibers in the web to one another, and the other being the ability to adhere the bonded portions of the web to the surface of the creping drum. In general, any material having these two capabilities may be utilized as the bonding material, if the material can be dried or cured to set it. Representative adhesive bonding materials which are capable of accomplishing both of these are emulsions of resins such as acrylates, vinyl acetates and styrene-butadiene. In other instances, the bonding material may comprise a mixture of several materials, one having the ability to accomplish interfiber bonding and the other having the ability to adhere the web to the creping surface. However, in either instance, the materials are preferably applied as an integral mixture to the same areas of the web.

Figure 5:
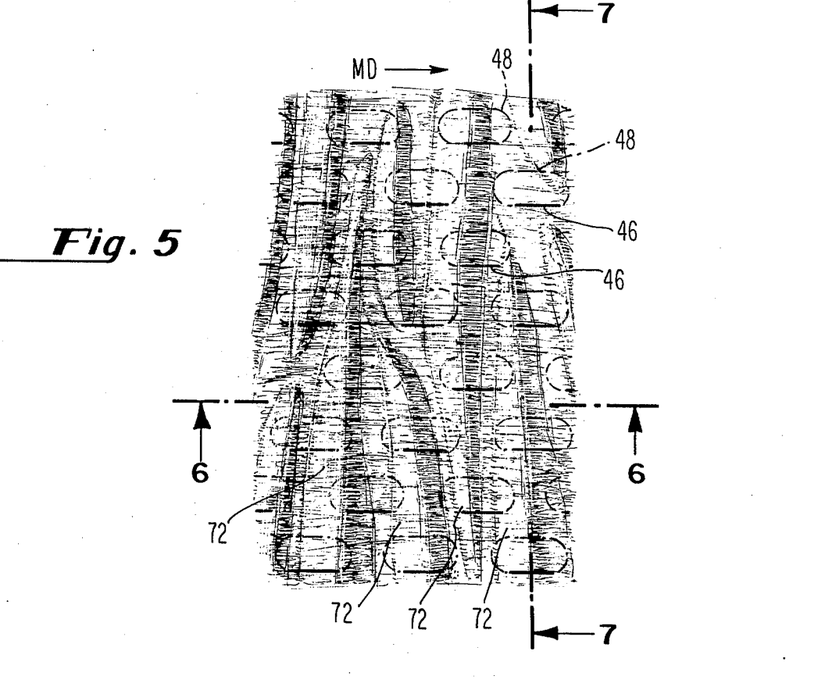
FIG. 5 is a greatly enlarged fragmentary plane view of the completed web of this invention.
Figure 6:
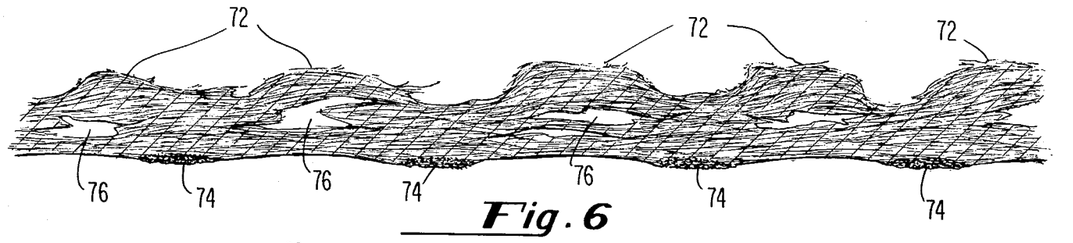
FIG. 6 is a sectional view along line 6—6 of FIG. 5.

Referring to FIGS. 5 and 6, the doctor blade 66 retards the motion of the web, and thereby causes the web to buckle to form coarse, transverse crepe ridges 72 which are most pronounced on the surface of the web which is unadhered to the creping drum. In other words the web is mechanically worked and foreshortened, and this enhances the softness and stretch of the web. Generally a fine crepe pattern can be perceived in the bonded areas 74. Due to the relatively high basis weight of the sheet (i.e. between about 25 and 100 lbs./2,880 ft.$^2$) the bulking of the web by the creping operation tends to cause internal splitting of the web, as indicated by numeral 76 in FIG. 6. This internal splitting is partially responsible for the enhancement of the bulk, softness and fluid holding capacity of the sheet.

Figures 7, 8:
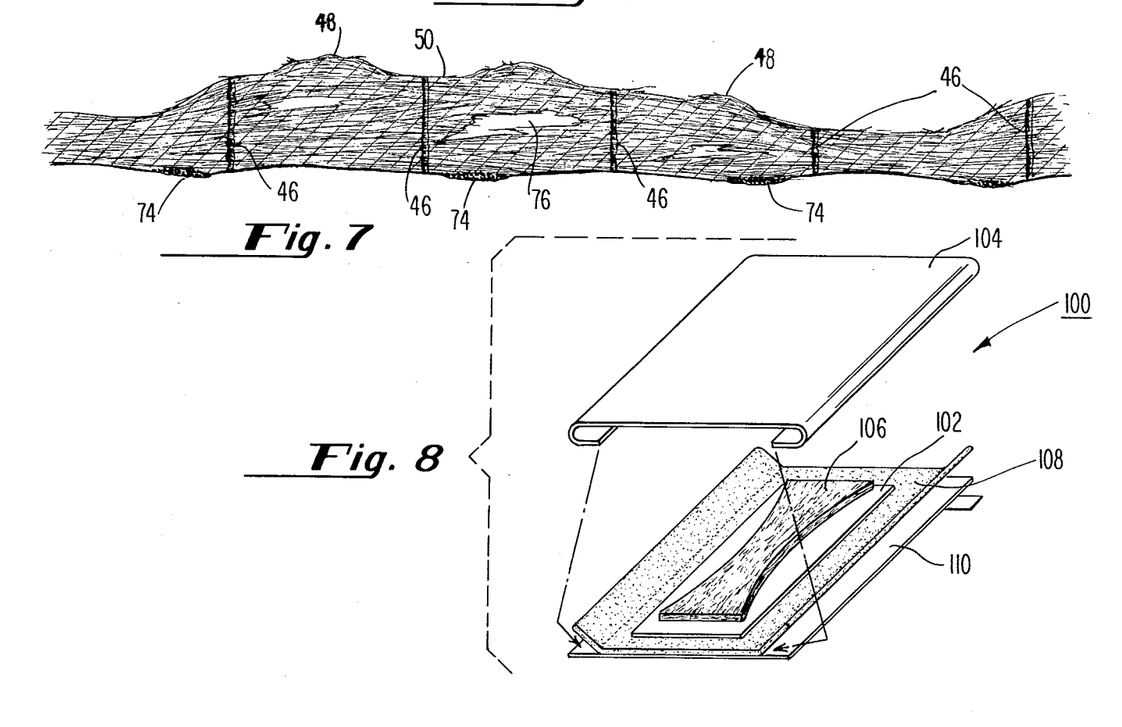
FIG. 7 is a sectional view along line 7—7 of FIG. 5.
FIG. 8 is a exploded isometric view of the preferred disposable diaper having a wicking layer provided by the fibrous web of this invention.

Referring to FIGS. 5 and 7, the absorbent web of this invention includes a plurality of crests 48 and valleys 50 on the surface opposite that which is adhered to the creping surface. This is the same surface which includes the coarse crepe ridges 72. The crests 48 and valleys 50 were formed in the web by the embossing operations, as can be seen in FIG. 4. However, the pattern of crests and valleys on the surface of the web which is adhered to the creping surface is substantially obliterated by the compacting action of the doctor blade 66 (see FIG. 7).

A plurality of cuts, or apertures, extend through the thickness of the web in spaced-apart areas. These cuts are generally elongated in the machine-direction of web formation, and are in an aligned, regular pattern (FIGS. 4 and 5). These cuts were also formed in the web by the embossing operation.

The fibrous web of this invention has a basis weight in the range from or about 25 to about 100 lbs./2,880 feet$^2$, a density of from about 0.08 grams/cc to less than about 0.16 grams/cc, a liquid holding capacity of greater than 500%, an absorbency rate of less than 2.5 seconds, a wicking rate of greater than 14 cm/10 minutes and wet-cross-machine-direction tensile strength of greater than 2 ounces/inch.

In the most preferred embodiment of this invention the creped fibrous web has a basis weight exceeding 50 lbs/2,880 feet$^2$; a density in the range of from about 0.08 grams/cc to less than about 0.13 grams/cc; a liquid holding capacity in excess of 700%; an absorbency rate of less than 1.5 seconds, a wicking rate of greater than 16 cm/10 minutes and a wet-cross-machine-direction tensile strength of greater than 4 ounces/inch.

The basis weight of the fibrous web of this invention was calculated according to TAPPI Standard T 410 os-61.

The density of the sheet is calculated by dividing its basis weight, in grams/cm$^2$, by its caliber or thickness, in centimeters. The thickness is measured according to ASTM D-1777 employing a Federal Bulker Thickness Gauge (Model Y-7227) with a foot area of 1 square inch and a weight of 235 grams.

The liquid-holding capacity is a measure of the amount of water that the fibrous web can absorb, and is determined as follows:

A fibrous web of known weight is attached at its edge to a ¼ inch rod by two pieces of tape and then is rolled up tightly and secured with a small piece of tape. The rolled-up fibrous web is positioned ½ inch from one end of the rod, and is then suspended for 1 minute in a 250 ml buret containing 250 ml of water. The sample is then lifted out of the water leaving the end of the sample inside the buret for 2 minutes to let excessive water drain off. Thereafter the sample is discarded, and the amount of water remaining in the buret is determined. The amount of water in the buret is subtracted from 250 (the original volume of water in the buret) to obtain the weight of water held by the web. The capacity is then reported as a percentage by employing the following equation:

$$\text{Capacity (\%)} = \frac{\text{Weight of Water in Sample}}{\text{Weight of Dry Sample}} \times 100$$

The absorbency is a measure of how fast water will pass through the surface of the web, and is determined by TAPPI Standard T 432 su-72 using a 1.0 ml drop of water. In this test the total volume of the drop must be absorbed into the sheet and no portion of the drop may pass through the sheet.

The wicking rate indicates how fast fluid will be transmitted within the plane of the web, and is calculated according to TAPPI Standard RC-8 with the water being at 69° Fahrenheit.

The wet cross-machine-direction tensile strength is measured according to TAPPI Standard T 404 os-74. Prior to conducting this test the sample is saturated with water, and the test is run within 30 seconds of saturation.

The fibrous web of this invention preferably has a cross-machine-direction stretch of no less than 10%, and most preferably no less than 14%. The stretch of the fibrous sheet is an indicator of how well the sheet will resist local stresses. Stating this another way, the energy which a fibrous web can absorb before breaking is a function of both the tensile breaking strength of the web and its stretch. Applicant has found that a fibrous web having the tensile strength and the elongation characteristics set forth above tend to resist tearing of the sheet when the sheet encounters energy levels which are generally imposed on wicking layers in disposable diapers.

The cross-machine-direction stretch of the fabric is determined according to TAPPI Standard T 457 os-46.

To the best of applicant's knowledge all prior art wet-formed sheets in the basis weight range of from about 25 to about 100 lbs./2,880 square feet are inferior to the fibrous web of this invention in one or more of the properties of fluid holding capacity, absorbency rate or wicking rate.

Referring to FIG. 8, the fibrous web of this invention is included in a disposable diaper 100 to function as a wicking layer 102. It should be understood that the fibrous web 102 may have other applications; however, its most preferred use is as a wicking layer in disposable diapers, and similar sanitary articles.

The disposable diaper 100 is of the type presently being sold by Scott Paper Company under the Trademark SCOT TOTS. That diaper is disclosed and claimed in U.S. Pat. No. 3,916,900, assigned to Scott Paer Company, and is incorporated by reference into the instant application.

The disposable diaper 100 is of a multilayer construction; including, (1) a moisture-impervious facing layer 104 adapted to be positioned in engagement with a wearer; (2) a low density fluff batt 106 of cellulosic fibers having a density of less than 0.08 grams/cc disposed beneath the facing layer 104 for absorbing and retaining body fluids which pass through the facing layer; (3) the fibrous web 102 of this invention positioned adjacent the lower surface of the fluff batt 106, and adapted to both retain and spread body fluids which pass through said fluff batt; (4) an elastomeric, wet-stable form layer 108 disposed beneath the fibrous web for confining and maintaining the fibrous material (the fluff batt and wicking layer) in the perineal region of the wearer, and (5) a moisture-impervious backing sheet 110, preferably in the form of a plastic layer, to prevent body fluids from striking through the backside of the diaper.

Most preferably the fibrous layer 102 has side margins which terminate short of the side margins of the diaper, and end margins which terminate short of the end margins of the diaper. This construction is desired because of the excellent wicking rate characteristics of the fibrous layer. Stating this another way, the fluid directed into the wicking layer 102 is readily transmitted to end and side margins thereof. If the end and side margins of the wicking layer extended to the end and side margins of the diaper, fluid leakage would most likely occur. Accordingly, to avoid the possibility of such leakage the discrete wicking layer 102 is positioned totally within the confines of the diaper structure.

Most preferably the wicking layer 102 is bonded and creped on only one side, and that side is positioned in the diaper facing away from the low density fluff batt 106. The unbonded surface of the web is placed in engagement with the fluff batt because it has a generally undulating configuration provided by the crests and valleys imparted to said surface in the embossing operation, and by the raised crepe ridges imparted to said surface by the creping operation. This undulating configuration provides high surface area exposure of the wicking layer to body fluids which pass through the fluff batt. This high surface area exposure to fluids enhances the absorbency rate through that surface of the wicking layer. Moreover, the undulating configuration functions to aid in stabilizing the fluff batt.

It should be understood that the wicking layer 102 of this invention can be employed in diapers other than that specifically described above. However, in order to properly function as a wicking layer it should have a greater density than the absorbent components disposed above it. Most preferably the wicking layer of this invention is employed in conjunction with a loosely compacted batt of separated cellulosic fibers having a density of less than 0.08 grams/cc.

What is claimed is:

1. A disposable sanitary product including a liquid-pervious facing layer adapted to be positioned in contact with a wearer, a low density batt of cellulosic fibers disposed beneath the facing layer for absorbing body fluids, and a fibrous wicking layer disposed beneath, and in engagement with said fibrous batt for aiding in distributing the flow of fluid within said product, the improvement wherein said wicking layer is an embossed and creped fibrous web formed from an aqueous slurry, and comprises:
    (a) randomly arranged and contacting sulfate wood pulp fibers constituting the predominate fiber component, by weight, of the web, said fibers being bonded together through a portion of the thickness of the web almost exclusively by papermaking bonds, said portion being substantially free of debonders and wet strength additives;
    (b) a plurality of fractured areas provided by embossing, said fractured areas being in the form of apertures extending through the web thickness, said apertures being disposed in spaced-apart areas which are substantially uniformly distributed throughout the web;
    (c) an adhesive bonding material extending only partially through the web thickness to form bonded regions having a greater strength than the portion of the web in which the fibers are bonded together almost exclusively by the papermaking bonds, said web being creped in regions containing bonding material to enhance web softness and to foreshorten the web to enhance its stretch;
    (d) said web having a basis weight of from about 25 to about 100 lbs./2,880 feet$^2$, a greater density than that of the fluff batt, said density being in the range of from about 0.08 grams/cc to less than about 0.16 grams/cc, a liquid holding capacity greater than 500%, an absorbency rate of less than 2.5 seconds, a wicking rate of greater than 14 cm/10 minutes, a minimum cross-machine-direction stretch of 10% and a wet cross-machine-direction tensile strength of greater than 2 oz./inch.

2. The disposable sanitary product according to claim 1, wherein said bonding material is disposed on only one side of the fibrous web, and the unbonded side of said web is positioned in engagement with the low density batt.

3. The disposable sanitary product according to claim 1, wherein said fibrous web has opposed side margins terminating inwardly of adjacent side margins of the product, and opposed end margins terminating inwardly of adjacent end margins of the product.

4. The disposable sanitary product according to claim 1, wherein said fibrous web has a density in the range of from about 0.08 grams/cc to less than about 0.13 grams/cc; a liquid holding capacity in excess of 700%; an absorbency rate of less than 1.5 seconds, a wicking rate of greater than 16 cm/10 minutes and a wet-cross-machine-direction tensile strength greater than 4 ounces/inch.

5. The fibrous web according to claim 4, wherein said basis weight is greater than 50 lbs./2,880 feet$^2$.

6. The fibrous web according to claim 5, having a minimum cross-machine-direction stretch of 14%.

7. The fibrous web according to claim 6, wherein the fibers are 100% sulfate wood pulp fibers.

8. A soft, absorbent, embossed and creped fibrous web formed from an aqueous slurry, said web comprising:
    (a) randomly arranged and contacting sulfate wood pulp fibers constituting the predominate fiber component, by weight, of the web, said fibers being bonded together through a portion of the thickness of the web almost exclusively by papermaking bonds, said portion being substantially free of debonders and wet strength additives;
    (b) a plurality of fractured areas provided by embossing, said fractured areas being in the form of apertures extending through the web thickness, said apertures being disposed in spaced-apart areas which are substantially uniformly distributed throughout the web;
    (c) an adhesive bonding material extending only partially through the web thickness to form adhesively bonded regions having a greater strength than underlying regions which are bonded together almost exclusively by the papermaking bonds, said web being creped in regions containing bonding material to enhance web softness and to foreshorten the web to enhance its stretch;
    (d) said web having a basis weight in the range of from about 25 to about 100 lbs./2,880 feet$^2$, a density of from about 0.08 grams/cc to less than about 0.16 grams/cc, a liquid holding capacity of greater than 500%, an absorbency rate of less than 2.5 seconds, a wicking rate of greater than 14 cm/10 minutes, a minimum cross-machine-direction stretch of 10% and a wet cross-machine-direction tensile strength of greater than 2 oz./inch.

9. The fibrous web according to claim 8, wherein one surface of the web is free of bonding material, and that surface has an undulating profile provided by a plurality of adjacent crests and valleys provided by embossing, and by spaced ridges provided by creping, said spaced ridges extending through the crests and valleys in a direction transverse to the machine direction of web formation.

10. The fibrous web according to claim 8, wherein said basis weight is greater than 50 lbs./2,880 feet$^2$.

11. The fibrous web according to claim 8, wherein the fibers are at least 80% sulfate wood pulp fibers.

12. The fibrous web according to claim 11, wherein the fibers are 100% sulfate wood pulp fibers.

13. The fibrous web according to claim 8, having a density in the range of from about 0.08 grams/cc to less than about 0.13 grams/cc; a liquid holding capacity in excess of 700%; an absorbency rate of less than 1.5 seconds, a wicking rate of greater than 16 cm/10 minutes and a wet-cross-machine-direction tensile strength greater than 4 ounces/inch.

14. The fibrous web according to claim 13, wherein said basis weight is greater than 50 lbs./2,880 feet$^2$.

15. The fibrous web according to claim 14, having a minimum cross-machine-direction stretch of 14%.

16. The fibrous web according to claim 15, wherein the fibers are 100% sulfate wood pulp fibers.

* * * * *